(12) United States Patent
Bednaz et al.

(10) Patent No.: US 8,376,741 B2
(45) Date of Patent: Feb. 19, 2013

(54) HANDLE FOR CRIMPABLE ORTHODONTIC ARCHWIRE STOP, ARCHWIRE ASSEMBLY AND METHOD OF USING

(75) Inventors: Alan J. Bednaz, Terryville, CT (US); Thomas B. Cameron, Avon, CT (US); Michael R. Spring, Unionville, CT (US)

(73) Assignee: Ultimate Wireforms, Inc., Bristol, CT (US)

( * ) Notice: Subject to any disclaimer, the term of this patent is extended or adjusted under 35 U.S.C. 154(b) by 440 days.

(21) Appl. No.: 12/454,605

(22) Filed: May 20, 2009

(65) Prior Publication Data

US 2010/0297570 A1 Nov. 25, 2010

(51) Int. Cl.
*A61C 7/02* (2006.01)

(52) U.S. Cl. .............................. 433/22; 433/3

(58) Field of Classification Search .................. 433/2, 3, 433/4, 5, 10, 11, 13, 14, 16, 17, 18, 19, 20, 433/21, 22, 24, 25, 58, 121, 141, 162, 147, 433/153; 81/427, 3.08, 177.1, 427.5, 489; 606/206, 225; 294/32, 92, 99.1; 16/110.1, 16/111.1; 72/458, 459, 479
See application file for complete search history.

(56) References Cited

U.S. PATENT DOCUMENTS

| | | | | |
|---|---|---|---|---|
| 3,922,786 A * | 12/1975 | Lavin | | 433/24 |
| 3,986,265 A * | 10/1976 | Cusato | | 433/4 |
| 4,571,179 A | 2/1986 | Balenseifen | | 433/20 |
| 4,583,944 A | 4/1986 | Hanson | | 433/22 |
| 4,639,219 A | 1/1987 | Gagin | | 433/22 |
| 4,764,112 A | 8/1988 | Bergersen | | 433/22 |
| 4,904,183 A * | 2/1990 | Hannan et al. | | 433/3 |
| 5,259,760 A | 11/1993 | Orikasa | | 433/20 |
| 5,306,142 A * | 4/1994 | Richards | | 433/22 |
| 5,542,842 A * | 8/1996 | Andreiko et al. | | 433/3 |
| 5,556,277 A | 9/1996 | Yawata et al. | | 433/17 |
| 5,562,445 A * | 10/1996 | DeVincenzo et al. | | 433/19 |
| 5,885,290 A * | 3/1999 | Guerrero et al. | | 606/71 |
| 5,910,008 A | 6/1999 | Tran | | 433/22 |
| 6,234,792 B1 * | 5/2001 | DeVincenzo | | 433/22 |
| 7,160,106 B2 | 1/2007 | Farzin-Nia et al. | | 433/22 |
| 2005/0191592 A1 * | 9/2005 | Farzin-Nia et al. | | 433/22 |
| 2007/0190477 A1 * | 8/2007 | Sheikh et al. | | 433/19 |

* cited by examiner

*Primary Examiner* — Cris L Rodriguez
*Assistant Examiner* — Justin O'Donnell
(74) *Attorney, Agent, or Firm* — Alix, Yale & Ristas, LLP (57) ABSTRACT

A handle for releasably retaining tubular sleeve-like crimpable stops is disclosed. The handle includes an elongated body with opposed ends and at least one receptacle positioned at one end of the body. The receptacle has an inside surface and defines an entry opening. The receptacle may be configured to mechanically retain the stop, or the stop may be releasably bonded to the receptacle by sticky substances like wax, any suitable adhesive or techniques such as heat bonding. The handle is molded from plastic in a color contrasting with the oral environment, such as orange. The handle aids in handling and positioning crimpable stops during installation of archwire assemblies in the oral environment. A stop retained in the disclosed handle is highly visible and can be handled without tools.

15 Claims, 11 Drawing Sheets

HANDLE FOR CRIMPABLE ORTHODONTIC ARCHWIRE STOP, ARCHWIRE ASSEMBLY AND METHOD OF USING

BACKGROUND

The present disclosure relates to stops commonly used on orthodontic archwires in combination with tooth-mounted orthodontic brackets for treatment of tooth alignment issues. More particularly, the present disclosure relates to assemblies of archwires and crimpable stops pre-threaded on the archwires.

Orthodontic treatment normally involves the application of mechanical forces to urge improperly positioned teeth into correct alignment. One common form of orthodontic treatment includes the use of orthodontic brackets that are fixed to teeth such as by a band around individual teeth or, more commonly, by mounting the brackets directly to the teeth. A resilient curved archwire is then seated in the archwire slots of the brackets. The archwires are generally attached to the brackets by ligature wires or elastic bands. Brackets of the self-ligating type include a movable cover that selectively closes the archwire slot of the brackets, eliminating the need for ligature wires or elastic bands. The movable cover is opened for inserting the archwire and then closed for retaining the archwire within the archwire slot. When a patient's teeth are out of alignment, the archwire elastically deforms to engage the brackets, thereby introducing a force that urges the teeth to move to the correct position over time.

A frequent problem observed during orthodontic treatment is that the archwire tends to move relative to the brackets under forces applied between the teeth, brackets and archwire in the oral environment. Unbalanced forces produced by the tongue, mouth muscles and chewing have a tendency to move the archwire laterally through the archwire slots of the brackets. This movement may cause a free end of the archwire to protrude from one of the brackets attached to the molars and contact gum or cheek tissue. As a result of the movement, the opposite free end of the archwire may also become disengaged from its bracket. The protruding ends of the archwire can irritate the gum or cheek tissue. Further, orthodontic treatment is disrupted by release of the archwires from the brackets.

Self-ligating brackets are constructed to retain the archwire without ligatures and elastic bands which inherently limit movement of the archwire relative to the brackets. In fact, the tooth movement promoted by free relative movement between archwire and bracket is an advantage of self-ligating brackets. Several conventional techniques are used to limit movement of the archwire in the bracket slots to prevent disengagement of the archwire from the brackets as well as to direct forces to one or more teeth. One such technique is to insert the archwire through a crimpable sleeve, such as a small diameter tube, then position the archwire within the archwire slots with the sleeve located between two adjacent brackets. The sleeve is eventually secured (crimped) to the archwire at a fixed position to form a stop. The sleeve is configured such that the sleeve cannot pass through or move beyond an archwire slot as the archwire moves in the lateral direction. In this manner, the maximum movement of the archwire is limited to the distance between the adjacent brackets. This arrangement effectively prevents the free ends of the archwire from becoming disengaged from the molars at the back of the mouth. Stops may be arranged to direct forces generated by the archwire to specific teeth.

A major shortcoming of the conventional technique described above is that the crimpable sleeve is mounted to the archwire in the field, such as a doctor's office, and usually by the dentist or a dental assistant. Archwires and crimpable sleeves are very small, making threading a sleeve onto the archwire difficult. The sleeves also have a tendency to slide off the archwire during handling and installation. The tiny sleeves are easily mishandled and/or lost.

There is a need for an improved archwire assembly that eliminates the need for field assembly and further limits the movement of the sleeve once positioned on the archwire.

There is a need for a simple, disposable tool for handling crimpable sleeves in the field.

There is also a need for an improved archwire assembly that improves the visibility of a crimpable sleeve on an archwire and facilitates manipulation of the sleeve into a desired location on the archwire.

SUMMARY

Several embodiments of a handle for crimpable stops are disclosed. A first embodiment mechanically retains stops in a receptacle. A second embodiment retains the stop by means of an adhesive, sticky substance, wax or combination thereof. Stops may also be retained by heating the handle material as discussed below. Handles may be connected to each other by various methods to form paired handle assemblies for use with archwires.

A handle for mechanically retaining tubular sleeve-like crimpable stops is disclosed. The handle includes an elongated body with opposed ends and at least one receptacle positioned at one end of the body. The receptacle has an inside surface and defines an entry opening. The inside surface is configured to surround a majority of the tubular sleeve and the receptacle is configured to elastically deform, thereby releasably retaining the tubular sleeve in the receptacle. The sleeve is received and released through the entry opening, which extends the length of the receptacle.

The handle and a received/retained crimpable stop form a handle assembly. The handle has a length at least approximately ten (10) times the diameter of a received stop. The handle may be molded from plastic in a color or combination of colors selected to contrast with the oral environment, such as orange. Other materials such as metal, wood/cellulose fiber, paper, plastic film or combinations of materials may also be suitable. The handle aids in handling and positioning crimpable stops during installation of archwire assemblies in the oral environment. A stop retained in the disclosed handle is highly visible and can be handled without tools.

One or more handle assemblies may be threaded on an archwire to form an archwire assembly. The archwire assembly is typically packaged for delivery to a customer. The handle has a length which produces off axis forces on the retained crimpable stop, which cause the stop to cant or cock relative to the archwire, producing temporary frictional engagement between the stop and the archwire. This frictional engagement prevents the stop or stops from sliding off the archwire during shipping and handling prior to installation.

The handle assembly and archwire assemblies are used in combination with a plurality of orthodontic brackets applied to a plurality of teeth, the archwire assembly comprising an archwire, at least one sleeve disposed on the archwire, and a handle having a first end defining a receptacle releasably engaged with the outside surface of the sleeve. An arm of the handle extends away from the receptacle and retained sleeve. In a typical orthodontic installation, the brackets are applied to a plurality of teeth and the handle is used to move the sleeves to selected positions on the archwire. The archwire is then secured to the orthodontic brackets and the handle is released from the sleeve by application of a force to the handle in a lateral direction. The sleeve is then crimped to the archwire to form a fixed stop.

DETAILED DESCRIPTION OF THE DISCLOSED EMBODIMENTS

A handle is constructed to receive and temporarily retain crimpable stops used in combination with orthodontic archwires. Also disclosed is an archwire assembly including an archwire and handles with received crimpable stops mounted thereon and a handle assembly including a handle and crimpable stop received therein. Paired handle assemblies are also disclosed. Several embodiments of handles, handle assemblies and archwire assemblies will be described with reference to FIGS. 1-15.

Crimpable stops are typically very small tubular devices (sleeves) made of soft temper tubing having a wall thickness of approximately 0.010". Stops are typically approximately 2 mm in length and have standardized inside and outside diameters on the order of 32 to 42 thousandths of an inch (0.032"-0.042"). A stop with an outside diameter of 0.032" typically has an inside diameter of about 0.020", while a stop with an outside diameter of 0.042" has an inside diameter of about 0.032". Crimpable stops may be square, rectangular, ovoid or cylindrical in cross section. Crimpable stops may be closed, to be threaded onto an archwire before the archwire is installed, or open, permitting the stop to be installed over an already installed archwire. An uncrimped stop may be used as a sliding spacer. When crimped to an archwire, the stop becomes a fixed point on the archwire. The disclosed handle facilitates handling of the tiny stops and also creates off axis forces which serve to temporarily frictionally retain the stop or stops on the archwire during shipping and installation.

Figure 14:
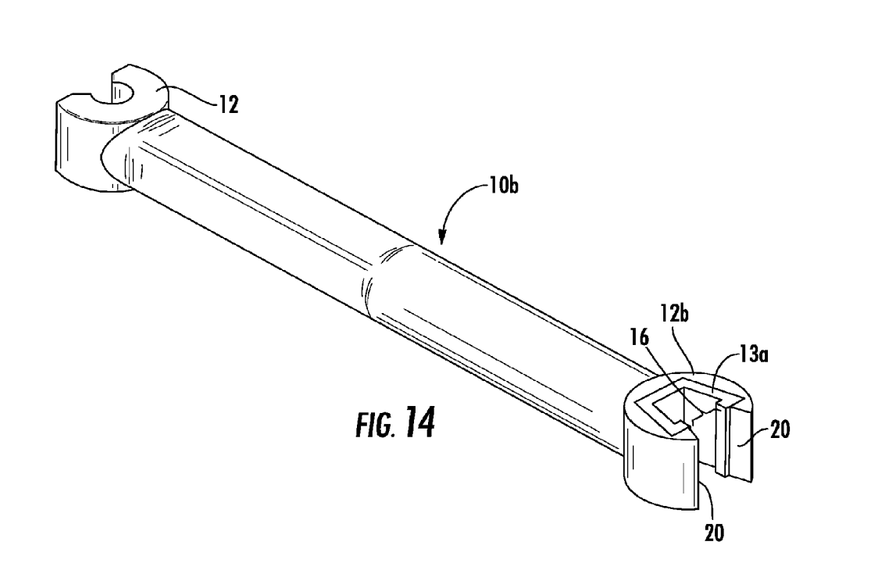
FIG. 14 is a perspective view of a further alternative embodiment of a handle for non-cylindrical stops and a received non-cylindrical stop according to aspects of the present disclosure.
Figure 15:
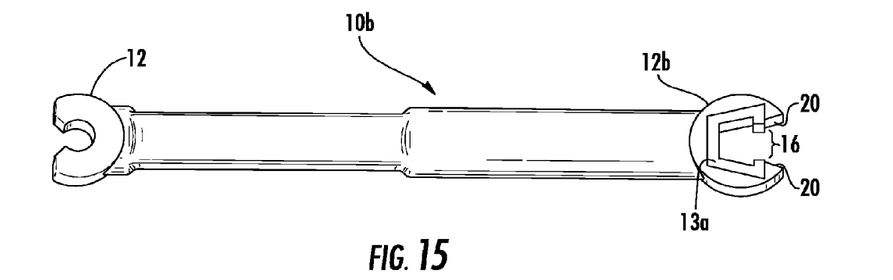
FIG. 15 is a side view of the handle and stop of FIG. 14.

With reference to FIGS. 1-4, a handle for crimpable stops is identified by the reference numeral 10. A disclosed exemplary embodiment of a handle 10 includes two receptacles 12, each configured to receive and releasably retain a single crimpable stop. The disclosed handle 10 is molded from polypropylene plastic, but alternative plastics or materials will occur to those skilled in the art. Other materials, such as metal, cellulose fiber, paper or plastic film materials may also be suitable. The selected material will have enough flexibility to permit the receptacle to flex when receiving and releasing a stop and sufficient rigidity to retain the stop. The first illustrated exemplary handle 10 is configured to work in combination with crimpable stops that are cylindrical in cross-section. Alternative receptacle configurations compatible with square or rectangular stops will occur to those skilled in the art, as illustrated in FIGS. 14 and 15. In the case of a cylindrical crimpable stop 13 shown in FIGS. 4-6, each receptacle 12 resembles the letter "C" in shape and includes an inside surface 14 having a cylindrical shape complementary to the cylindrical outside surface 15 of the stop 13. Each receptacle 12 defines an entry opening 16 extending the length 18 of the receptacle. Entry surfaces 20 along the length 18 of the entry opening 16 guide the stop 13 into the receptacle and promote suitable flexure of the receptacle as discussed below.

Figure 5:
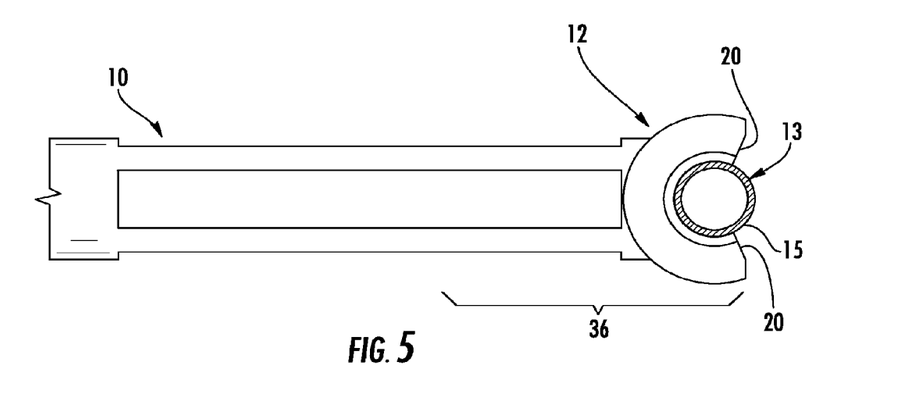
FIG. 5 is an enlarged, partial view of the handle for crimpable stop of FIGS. 1-3 in combination with a crimpable stop and archwire (shown in section)
Figure 6:
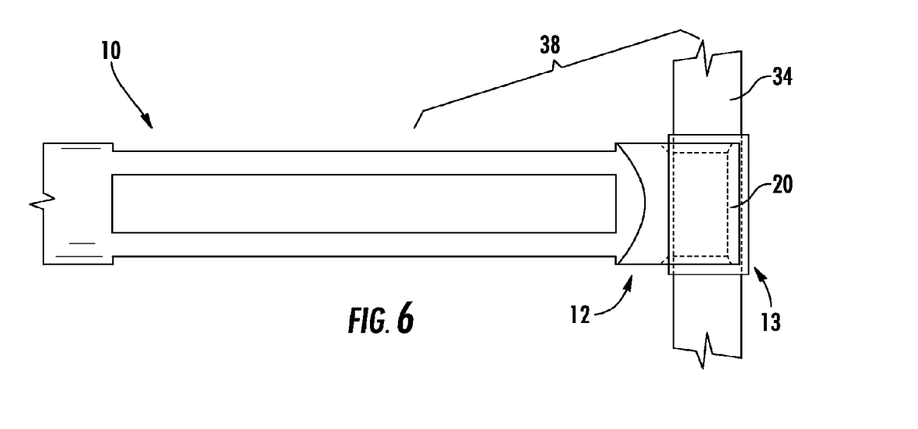
FIG. 6 is a top view of the handle for crimpable stop, crimpable stop and archwire combination of FIG. 5.

The receptacles 12 in the disclosed handle 10 have an inside surface 14 configured to extend greater than 180° around a received stop 13 as shown in FIG. 5. This configuration serves to retain a received stop 13 securely in the handle 10 until sufficient force is imposed upon the stop to remove it. The disclosed receptacles include inside surfaces 14 which subtend an angle of between approximately 230° and 270°, although any angular extent in excess of 180° may be suitable. Each receptacle has a length 18 slightly less than the length of a typical stop 13 (about 2 mm). This configuration permits end portions of the stop 13 to protrude from either side of the receptacle 12 as shown in FIG. 6, aiding in visual positioning of the stop.

Figure 4:
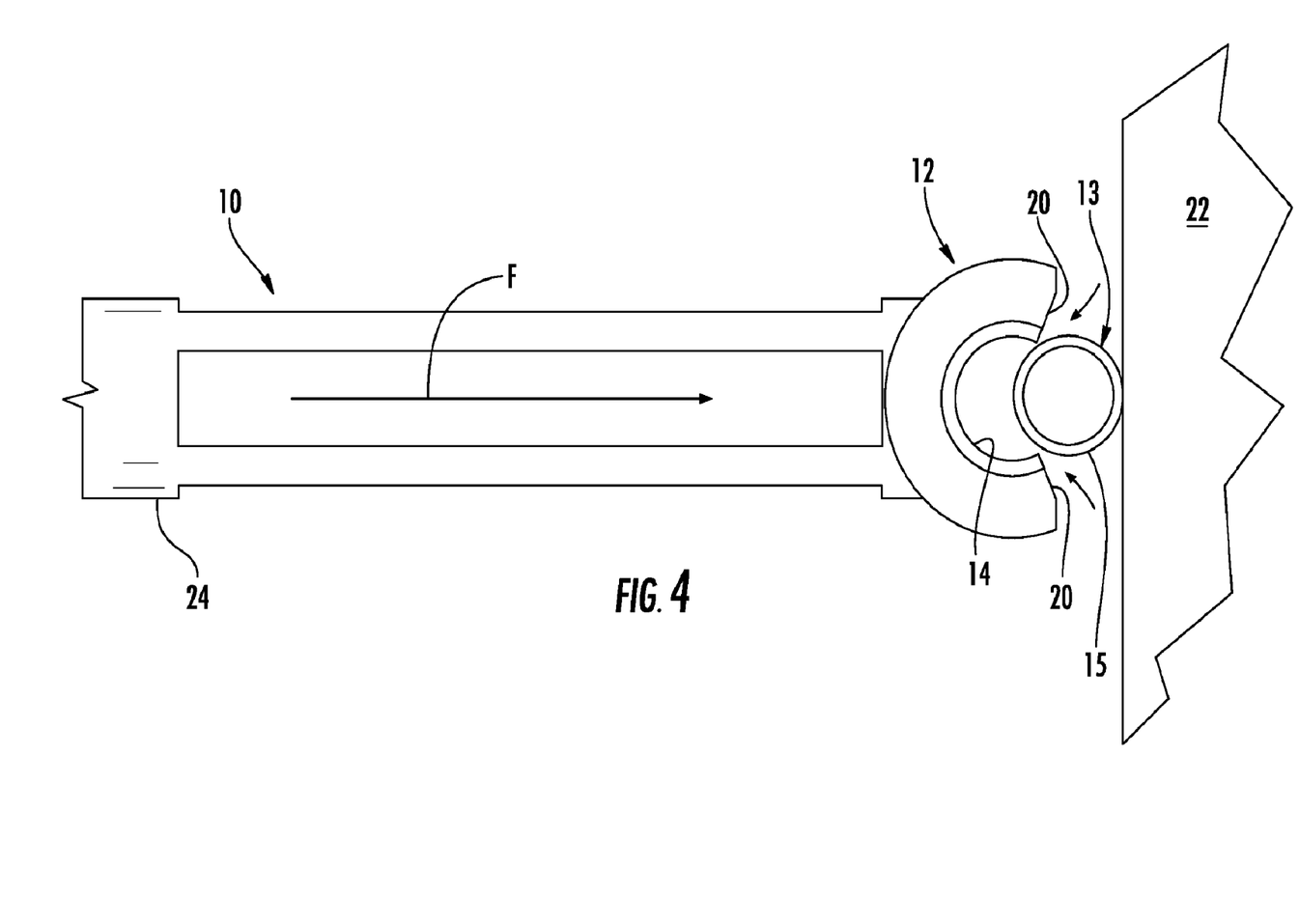
FIG. 4 is an enlarged, partial view of a handle for crimpable stop of FIGS. 1-3 receiving a crimpable stop according to aspects of the present disclosure.

With reference to FIG. 4, a cylindrical stop 13 resting on a hard surface 22 can be inserted into the receptacle 12 by placing the entry opening 16 above the stop with the stop generally parallel with the entry opening of the receptacle. Downward pressure F on the handle 10 brings the outside surface 15 of the stop 13 into contact with the entry surfaces 20 adjacent the entry opening 16 and causes flexure of the receptacle 12 until the stop is received in the receptacle as shown in FIG. 5. Once received in the receptacle 12, the stop 13 is releasably retained by elastic return of the receptacle toward its previous shape.

Figure 1:
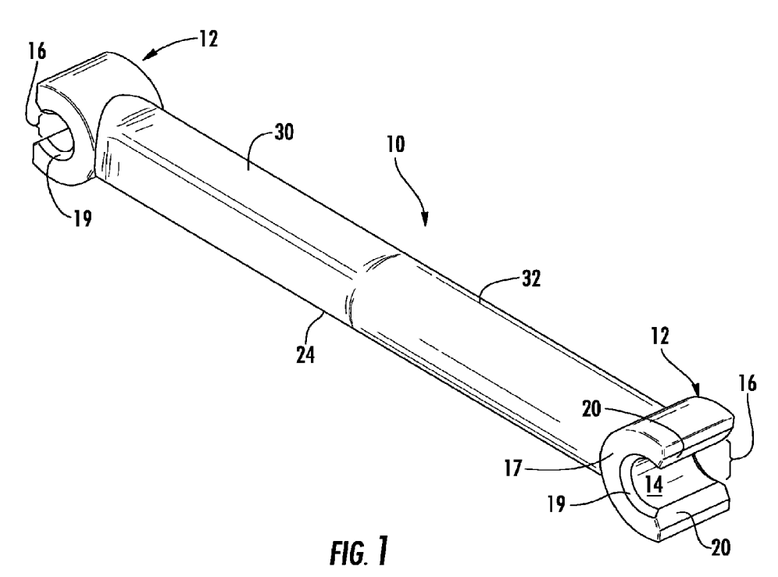
FIG. 1 is a perspective view of a handle for crimpable stop according to aspects of the present disclosure.
Figure 2:
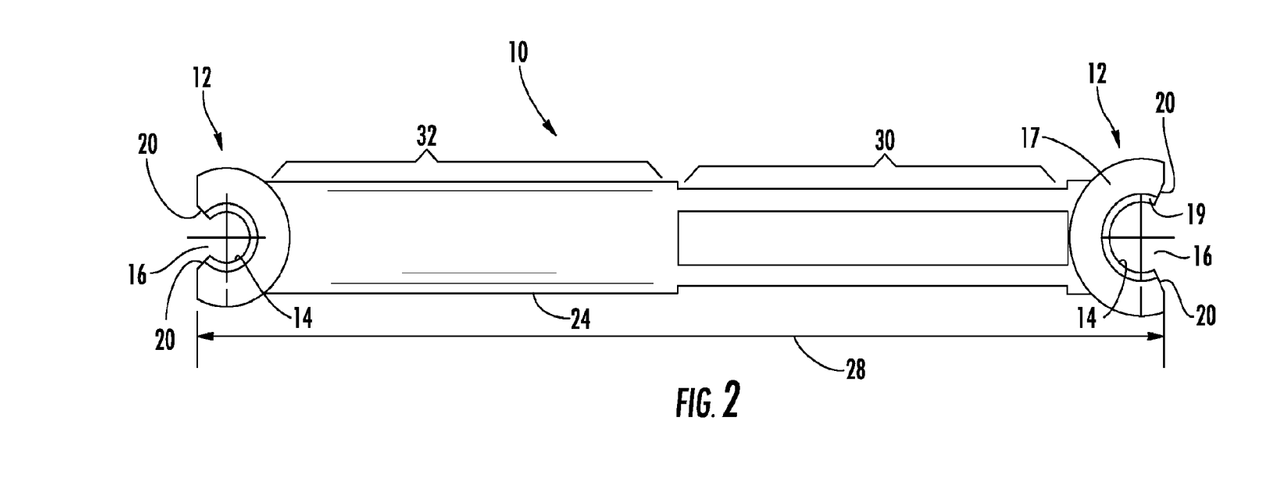
FIG. 2 is an enlarged side view of the handle for crimpable stop of FIG. 1.
Figure 3:
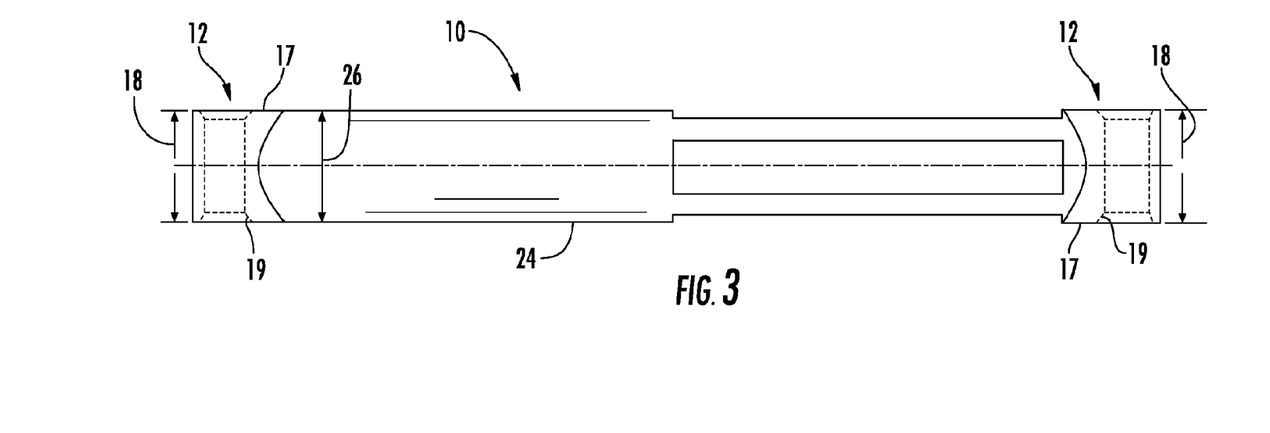
FIG. 3 is an enlarged top view of the handle for crimpable stop of FIG. 1.

With reference to FIGS. 1-3, the end faces 17 of the receptacles 12 include "C" shaped beveled surfaces 19. The open ended receptacle configuration and the beveled surfaces 19 facilitate insertion of a stop 13 into the receptacle from either end, rather than through the entry opening 16. Beveled surfaces 19 guide the end of a stop 13 into the receptacle during insertion.

The first disclosed embodiment of the handle 10 has two ends, each defining a receptacle 12. One end has a receptacle configured for a cylindrical stop having a 2 mm length and an outside diameter of approximately 0.042". The other end includes a receptacle 12 configured for a cylindrical stop having a 2 mm length an outside diameter of approximately 0.032". An arm or shaft 24 extends between the two receptacles 12. In the disclosed embodiment, the outside diameter 26 of the shaft 24 is approximately 0.065" (1.65 mm) and is the same as the length 18 of the receptacles 12. It will be noted that the length 18 of the receptacles is about 0.35 mm shorter than the length of the typical 2 mm stop. The overall length 28 of the handle 10, including the receptacles, is approximately 0.6".

The small size of the handle 10 and the receptacles 12 can make it difficult to visually identify which receptacle is configured for a large stop (0.042") and which receptacle is configured for a small stop (0.032"). The disclosed handle 10 uses different cross sectional shapes to assist the user in distinguishing one receptacle from the other. In the embodiment shown in FIG. 1, the square portion 30 of the shaft 24 corresponds to the small receptacle and the cylindrical portion 32 of the shaft 24 corresponds to the large receptacle. This configuration could be reversed, with the square portion of the shaft adjacent the small receptacle and the cylindrical portion of the shaft adjacent the large receptacle as shown in FIGS. 2 and 3. Alternative shaft sectional shapes, such as triangular, rectangular, hexagonal, etc. are also compatible with the disclosed handle and assemblies. Other means of identifying the large and small receptacles will occur to those skilled in the art. For example, the different ends of the handle may be different colors. Alternatively, the outside shape of one receptacle may be distinct from the other.

Figure 7:
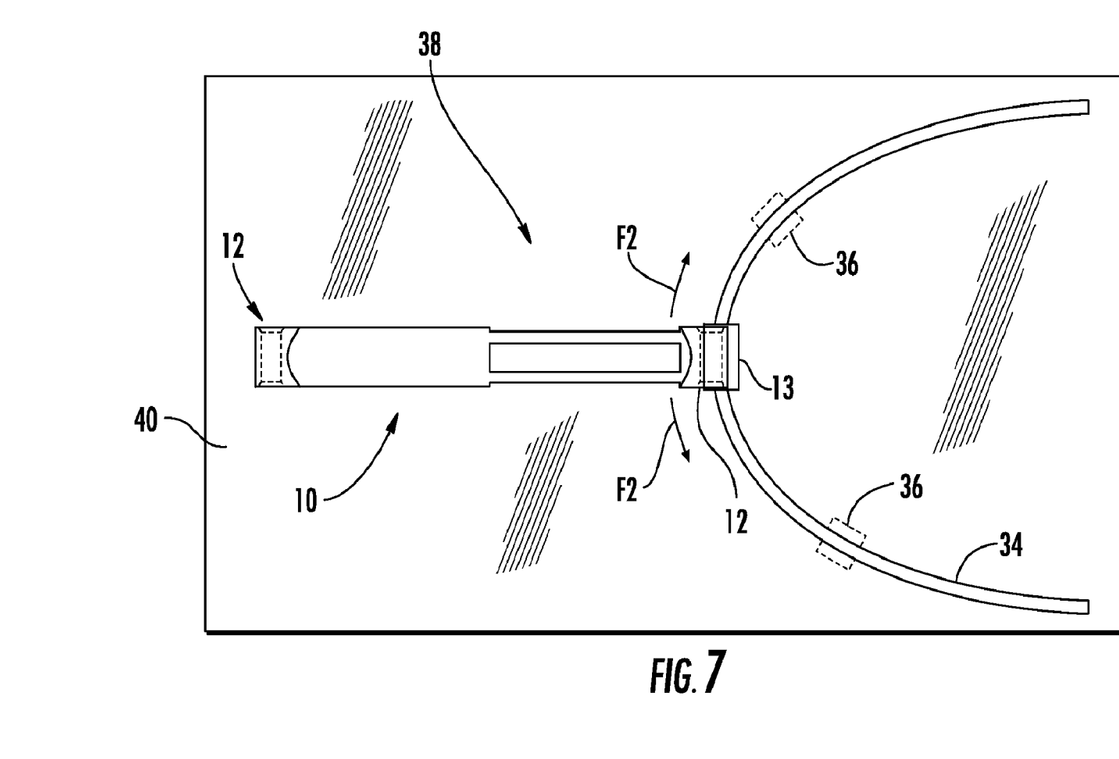
FIG. 7 is a top plan view of an archwire assembly including a handle for crimpable stop, crimpable stop and archwire according to aspects of the present invention. The crimpable stop and handle are enlarged for clarity.

The disclosed handle 10 has an overall length 28 of about 0.6", or approximately 15 times the diameter of the large stop and 20 times the diameter of the small stop. The length of the handle should be sufficient to allow for easy manipulation of the handle without tools. A length at least approximately ten (10) times the diameter of a stop 13 should be sufficient to allow a handle to function as described herein. One function of the disclosed handle is to allow a user to easily grasp the handle and use it to position the tiny and light-weight crimpable stops 13. A second function of the disclosed handle 10, illustrated in FIG. 7, is that it has sufficient length and mass to exert some force (torque) F2 on the stop where the force F2 is not parallel with the center line of the tubular body of the stop 13. When the assembled handle 10 and stop 13 are mounted on an archwire 34 as shown in FIG. 7, the off axis forces F2 generated by the handle 10 cause the tubular body to cock or cant relative to the archwire 34, thereby providing temporary frictional engagement between the stop 13 and the archwire 34. Such frictional engagement reduces unintended movement of the stop 13 relative to the archwire 34 when the archwire and stop are in positions where the stop would ordinarily tend to slide along the archwire 34 under its own weight in the absence of such frictional engagement.

The disclosed handle 10 may be sold separately as a disposable tool for use in orthodontic practice, as a handle assembly 36 with a crimpable stop pre-installed in one of the receptacles as shown in FIG. 5, or as part of an archwire assembly 38 including an archwire and one or more crimpable stops, each with a handle 10 attached as shown in FIG. 7. Any of these variants will typically be packaged in a plastic bag or sleeve 40 with a label identifying the archwire product, its size, shape or other attributes. FIG. 7 includes boxes positioned on either side of the handle 10 and stop 13 to illustrate additional handle assemblies 36 (handles 10 with received stops 13) pre-mounted on the archwire 34 to form an archwire assembly 38.

With respect to an archwire assembly with pre-threaded crimpable stops 13 and no means of retaining the stops on the archwire, the stops will typically slide off the arch wire 34 during shipping or manipulation during installation. The stops must then be re-installed in the field prior to installation of the archwire assembly. Field installation of stops 13 on an archwire 34 is time consuming and problematic due to the tiny size of the stop. As discussed with reference to FIG. 4, stops are easily placed in a receptacle 12 of the handle 10. Once received in the receptacle 12, a stop 13 is highly visible and can be handled without tools. The handle 10 facilitates threading a stop onto an archwire 34 by allowing the user to easily grasp and orient the stop relative to the archwire. Further, in an archwire assembly 38 where one or more handles 10 with received stops 13 are threaded on an archwire 34 prior to shipping to an orthodontist, the handle 10 acts to reduce movement of the stop 13 along the archwire during shipping or pre-installation handling in the field. If a handle 10 and received stop 13 does work its way off the archwire prior to installation, the stop 13 will be retained in the handle 10 and easily picked up and reinstalled.

FIG. 5 is an enlarged view of a handle 10 in combination with a received stop 13 forming a handle assembly 36. In a typical installation, the stop 13 is installed in the handle 10 as described with respect to FIG. 4. The handle 10 is then used to hold the stop 13 while the stop is threaded onto an archwire 34 forming an archwire assembly 38 as illustrated in FIGS. 6 and 7. The archwire assembly 38 may be packaged in a plastic bag or sleeve 40 and labeled for delivery to an orthodontist. A typical archwire assembly 38 may include one or more handles and received stops (handle assemblies 36) pre-threaded on an archwire as shown schematically in FIG. 7.

Figure 8:
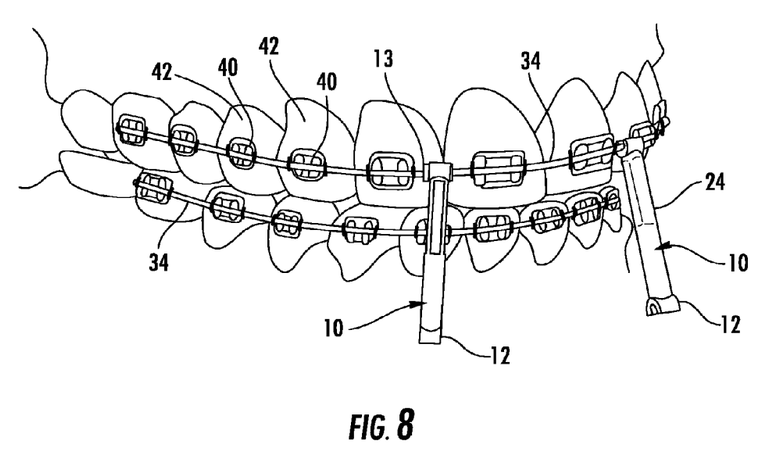
FIG. 8 shows an archwire system including handle assemblies according to the disclosure being used in combination with a plurality of orthodontic brackets mounted to a plurality of teeth.

The handle 10 firmly retains the stop 13 in its receptacle 12. The elongated shape of the handle 10 produces off axis forces F2 on the stop 13, which tend to prevent free movement of the stop along the archwire 34 during shipping and handling. During installation of an archwire assembly, the handle 10 clearly identifies the location of each stop 13 and facilitates positioning of the stops in a desired location on the archwire 34. In the absence of a handle 10, the tiny metallic stops 13 can be difficult to locate visually and typically require the use of a tool for positioning. Once the archwire assembly 38 is installed in an orthodontic bracket system and the archwire is securely retained by the brackets as shown in FIG. 8, a light force on the handle in a direction away from the archwire 34 will disengage the handle 10 from the stop 13. With the handle 10 removed, the stop 13 can then be crimped onto the archwire 34 using tools and techniques known in the art.

The handle 10 may be molded of plastic having a color, or combination of colors, which contrast with those colors generally found in the orthodontic setting. One color which has proven highly visible in the orthodontic setting is orange as shown in FIG. 8. Such coloration can assist in visually locating the handle and received stop against the background of a patient's mouth.

As shown in FIG. 8, the disclosed handle assembly 36 and archwire assembly 38 are used in combination with a plurality of orthodontic brackets 40 applied to a plurality of teeth 42, the archwire assembly 38 comprising an archwire 34, at least one stop 13 disposed on the archwire 34, and a handle 10 having a first end defining a receptacle releasably engaged with the outside surface of the stop 13. An arm 24 of the handle 10 extends away from the receptacle 12 and retained stop 13. In a typical orthodontic installation, the brackets 40 are applied to a plurality of teeth 42 and the handle 10 is used to move the stops 13 to selected positions on the archwire. The archwire is then secured to the orthodontic brackets 40 and the stop 13 is then released from the handle 10 by application of a force to the handle in a direction away from the archwire 34. The stop 13 is then crimped to the archwire 34 to form a fixed stop in a manner known in the art.

The disclosed handle 10 includes receptacles with inside surfaces 14 configured to closely match the outside surface 15 of a received cylindrical stop 13. Such a configuration is not necessary to accomplish the objectives of the disclosure. An open receptacle configuration having two or more semi-ring shaped arms configured to surround a majority of a stop and retain the stop in the receptacle may also achieve the objectives of the disclosure. The inside surface 14 of the receptacle 12 need not be a regular shape as illustrated, but could be irregular, including ribs, bumps or the like. All that is required is a receptacle configured to receive and mechanically retain a stop with sufficient force that the handle and stop remain together until the archwire assembly is installed in an orthodontic bracket system.

Figure 12:
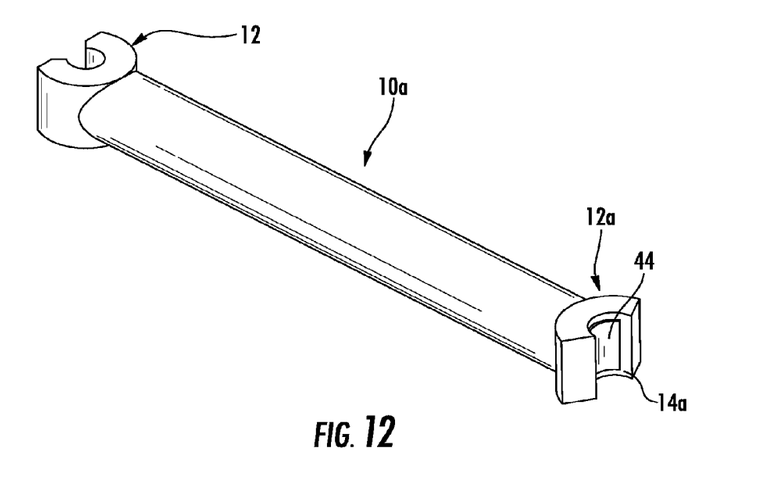
FIG. 12 is a perspective view of an alternative handle for crimpable stops according to aspects of the present disclosure.
Figure 13:
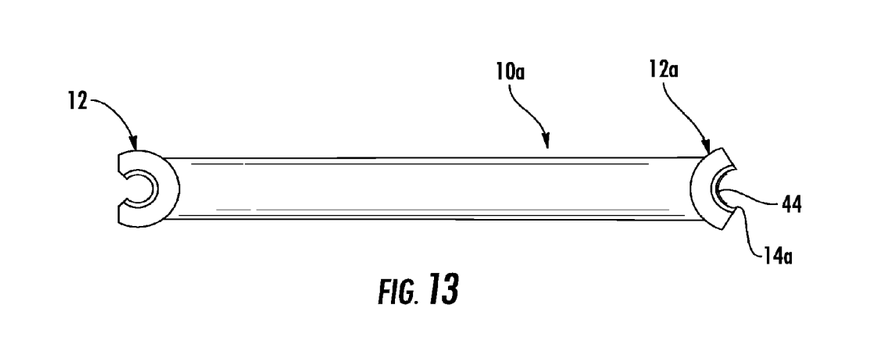
FIG. 13 is a side plan view of the handle for crimpable stops of FIG. 12.

In an alternative handle configuration shown in FIGS. 12 and 13, the receptacle 12a may be configured as a trough or saddle which does not surround more than one half of the circumference of the stop 13. In this alternative configuration, the inside surface 14a of the receptacle 12a may be provided with adhesive or sticky substance 44 to retain a received stop 13. The adhesive 44 may be of the type having a primary bond with the receptacle and a temporary or releasable bond with the stop. Sticky substances, such as dental wax may be used to adhere the stop to the receptacle 12a. Heat may be employed to partially melt the material of the receptacle 12a, an adhesive or a wax material to releasably bond a stop 13 to the receptacle 12a. Once the stop 13 is joined to the handle 10a to form a handle assembly 36, the handle 10a and stop behave in a manner described above. When installation of an archwire and stop is complete, force is applied to the handle 10a to break the bond between the handle 10a and the stop.

Figure 9:
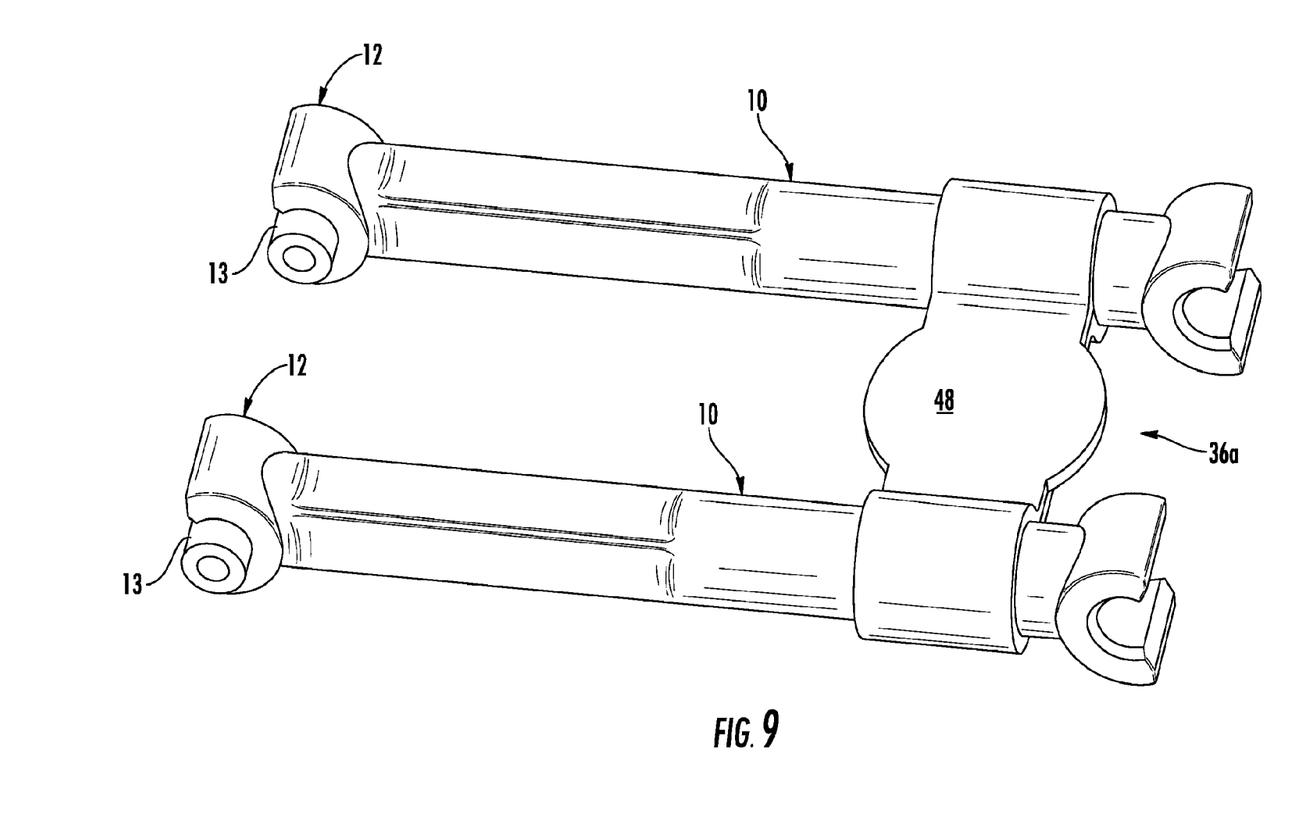
FIG. 9 is a perspective view of two handle assemblies according to the disclosure, connected by a removable attachment between the handle shafts according to aspects of the disclosure.
Figure 10:
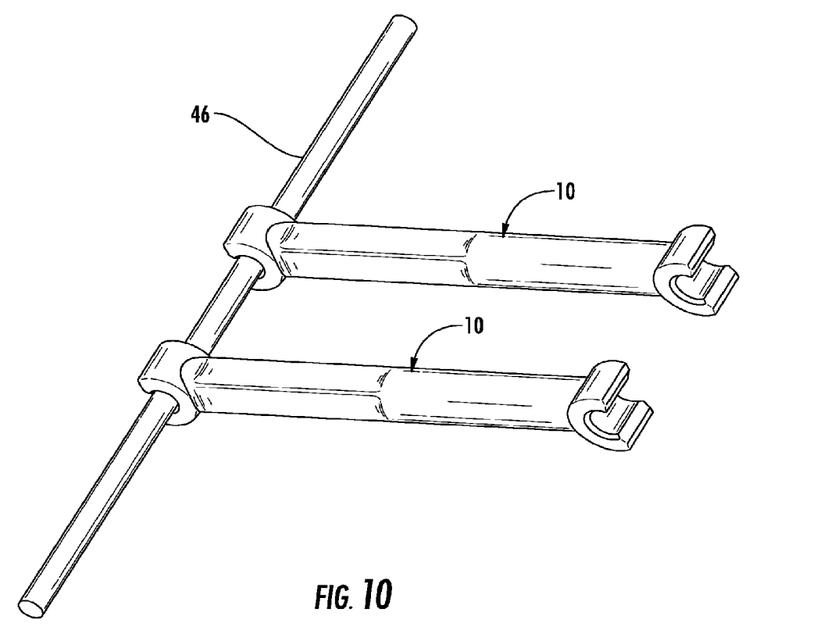
FIG. 10 is a perspective view of two handles according to the disclosure, connected by a rod extending through one of the handle receptacles according to aspects of the disclosure.
Figure 11:
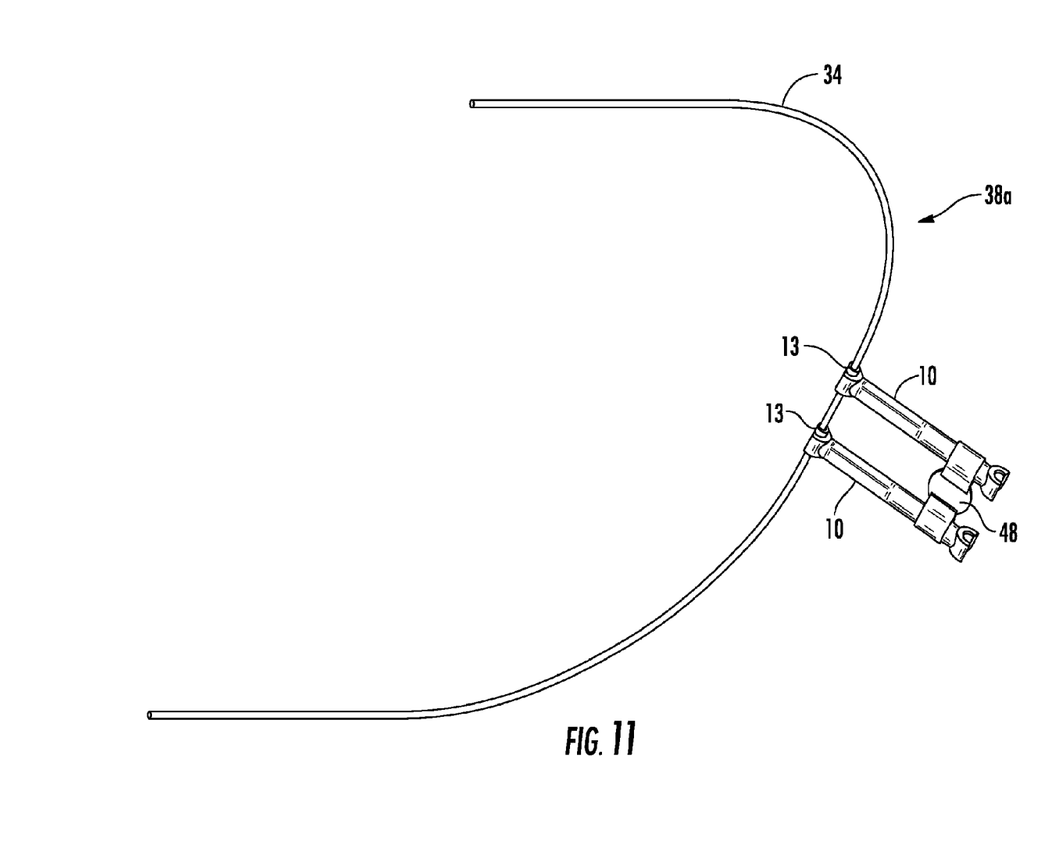
FIG. 11 is a perspective view of the connected handle assemblies of FIG. 9 on an archwire, forming an archwire assembly according to aspects of the disclosure.

The free ends of adjacent handles 10 in archwire assemblies 38 and 38a may be connected by a removable rod 46 as shown in FIG. 10, a paper or plastic tab 48 as shown in FIGS. 9 and 11 or adhesive (not shown). Such configurations help retain the handles 10 and stops 13 in position on the archwire 34 during shipping and handling. The connecting device 46, 48 may be configured to exert torque on the stops 13 to frictionally engage them with the archwire 34.

FIGS. 14 and 15 illustrate a further embodiment of a handle 10b for non-cylindrical orthodontic stops 13a according to aspects of the present invention. Some orthodontic stops 13a are split longitudinally to allow the stop to be placed over an archwire 34 when the archwire is installed in a set of orthodontic brackets. The handle 10b illustrated in FIGS. 14 and 15 includes a receptacle 12b configured to receive a non-cylindrical split stop 13a, forming a handle assembly 36a. The illustrated receptacle 12b includes an inside surface configured to closely match the outside surface configuration of the split stop 13a. As previously discussed, such a close match between the outside surface of the stop and the inside surface of the receptacle is not necessary to retain the stop according to the disclosure. The receptacle may be discontinuous in its longitudinal direction, taking the form of two or more arms configured to surround a majority of and frictionally engage the stop. The receptacle 12b defines an entry opening 16 between entry surfaces 20 configured to guide the split stop 13a into the receptacle 12b.

Some stops (not shown) are equipped with a hook or a ball extending from the outside surface, and a discontinuous receptacle configuration would make it possible to receive such a stop. When the split stop 13a is positioned over an archwire, a crimping tool may be applied to the outside of the receptacle 12b to close the stop over the archwire. Once the split stop 13a is at least partially closed over the archwire, the handle 10b may be removed by applying a force to the handle in a direction away from the archwire.

The description of disclosed embodiments is not intended to restrict or in any way limit the scope of the appended claims to the disclosed configurations. Additional advantages and modifications will occur to those skilled in the art. The claims are intended to encompass these broader aspects of the disclosure and are not limited to the specific details of the disclosed apparatus and illustrations shown and described. Accordingly, departures may be made from the details of the disclosed embodiments without departing from the scope of the claims.

The invention claimed is:

1. An orthodontic archwire assembly comprising:
   an archwire having a length between free ends;
   at least one sleeve disposed on said archwire, said sleeve having a longitudinal axis, an outside surface and an inside surface defining a longitudinal opening configured to permit said sleeve to slide freely along the length of said archwire; and
   a unitary handle having a first end defining a receptacle releasably engaged with the outside surface of said sleeve and an arm extending axially away from the receptacle and in substantially fixed relationship thereto and wherein said receptacle is oriented coaxial with the longitudinal axis of said sleeve and said arm is oriented transverse to the longitudinal axis of said sleeve and said receptacle,
   wherein said receptacle exerts retention forces on said sleeve in a direction not parallel with said longitudinal axis, said force having a magnitude sufficient to longitudinally alter the position of said sleeve with respect to said archwire and cause temporary, releasable frictional engagement between said sleeve and said archwire.

2. The orthodontic archwire assembly of claim 1, wherein said sleeve has an outside diameter and said arm has a length, said length being at least approximately 10 times said outside diameter.

3. The orthodontic archwire assembly of claim 1, wherein the outside surface of said sleeve is cylindrical and said receptacle is defined by an inside surface configured to frictionally engage the outside surface of said sleeve.

4. The orthodontic archwire assembly of claim 1, wherein the outside surface of said sleeve is cylindrical and said receptacle is defined by a complementary inside surface subtending an arc of greater than 180°.

5. The orthodontic archwire assembly of claim 1, wherein said receptacle has a second longitudinal axis substantially coincident with said sleeve longitudinal axis and a receptacle length measured parallel with said second longitudinal axis, said receptacle defining an entry opening extending the length of said receptacle.

6. The orthodontic archwire assembly of claim 5, wherein said entry opening is defined between substantially planar entry surfaces.

7. The orthodontic archwire assembly of claim 6, wherein each said entry surface is located in a plane including said second longitudinal axis.

8. The orthodontic archwire assembly of claim 5, wherein said entry surfaces define an obtuse included angle.

9. The orthodontic archwire assembly of claim 1, wherein said handle includes one or more colors selected to enhance visibility.

10. The orthodontic archwire assembly of claim 1, wherein the outside surface of said sleeve is releasably bonded to said receptacle by an adhesive, tacky substance, wax or heat bonding.

11. A method of using an archwire assembly in combination with a plurality of orthodontic brackets applied to a plurality of teeth, the archwire assembly comprising an archwire, at least one sleeve disposed on said archwire, and a handle having a first end defining a receptacle releasably engaged with the outside surface of said sleeve and an arm extending axially away from and oriented transverse to the receptacle, said method comprising:

applying the plurality of orthodontic brackets to the plurality of teeth;

using said handle to move said at least one sleeve to a selected position on said archwire;

securing the archwire assembly to the plurality of orthodontic brackets; and releasing said handle from said sleeve by application of force to said arm in a mesial or buccal direction.

12. The method of claim 11, comprising the step of:

crimping said sleeve to said archwire after releasing said handle from said sleeve.

13. A handle assembly for use in an orthodontic system having an archwire, comprising:

a unitary handle having an elongated body with opposed ends and at least one receptacle positioned at one end of said body, said elongated body extending axially away from said receptacle and in fixed relationship thereto, said receptacle having an inside surface, open longitudinal ends and defining an entry opening extending between said open longitudinal ends and said entry opening oriented transverse to the elongated body; and a tubular sleeve having an outside surface and a length, said sleeve disposed in said receptacle and releasably retained therein, wherein said sleeve is longitudinally manipulable along the archwire.

14. The handle assembly of claim 13, wherein said inside surface has a configuration complementary to a configuration of said outside surface and said receptacle is adapted to surround more than one half of said tubular sleeve, thereby mechanically releasably retaining said sleeve in said receptacle.

15. The handle assembly of claim 14, wherein the outside surface of said sleeve is releasably bonded to the inside surface of said receptacle by a sticky substance, wax, adhesive or heat applied to said inside surface.

* * * * *